United States Patent [19]

Longley et al.

[11] Patent Number: 4,540,807

[45] Date of Patent: Sep. 10, 1985

[54] AROMATIC BASE POLY-SULFOSUCCINATE ESTERS

[75] Inventors: Kermit D. Longley, Park Forest; Anastasios Karalis, Chicago, both of Ill.

[73] Assignee: Witco Chemical Corporation, New York, N.Y.

[21] Appl. No.: 307,340

[22] Filed: Sep. 30, 1981

[51] Int. Cl.$^3$ ............................................. C07C 143/12
[52] U.S. Cl. .................................... 560/151; 252/354; 524/747; 524/748; 524/832; 544/110
[58] Field of Search ................. 560/151; 544/110; 252/354

[56] References Cited

U.S. PATENT DOCUMENTS

| | | | |
|---|---|---|---|
| 2,028,091 | 1/1936 | Jaeger | 260/106 |
| 2,176,423 | 10/1939 | Jaeger | 560/151 |
| 2,507,030 | 5/1950 | Lynch | 560/151 |
| 2,887,504 | 5/1959 | Carnes et al. | 560/151 |
| 3,002,994 | 10/1961 | Williams et al. | 560/151 |
| 3,246,023 | 4/1966 | Shen et al. | 560/151 |
| 3,268,563 | 8/1966 | Shen et al. | 560/151 |
| 3,481,973 | 12/1969 | Wygant et al. | 560/190 |
| 3,640,842 | 2/1972 | Hullinger et al. | 162/175 |
| 3,682,845 | 8/1972 | Longley et al. | 260/2.5 AP |
| 4,117,237 | 9/1978 | Longley et al. | 560/151 |
| 4,154,955 | 5/1979 | Longley et al. | 560/151 |
| 4,250,050 | 2/1981 | Asbeck et al. | 560/151 |
| 4,299,975 | 11/1981 | Asbeck et al. | 560/151 |

Primary Examiner—Vivian Garner

[57] ABSTRACT

Di- and other poly-sulfosuccinate esters of di- and other poly-hydroxyl aromatic propoxylated compounds in which, by way of illustration, both of the hydroxyl groups of a bisphenol, for instance, Bisphenol A, are etherified with a propylene oxide α-epoxide, the free hydroxyl groups of the resulting propoxylated bisphenol then being esterified with a sufficient amount of maleic anhydride whereby the resulting intermediate acid ester compound comprises di- and/or poly-maleic acid esters having free carboxyl groups which are then esterified with propylene oxide α-epoxide to produce a further intermediate having a free hydroxyl group at each of its terminal ends; and after which said last-mentioned intermediate is reacted to introduce at least two sulfosuccinated groups into the final compound, for instance, by reaction with aqueous bisulfite. Before treatment with bisulfite, the alkoxylated maleic acid ester having free hydroxyl groups can again be esterified with maleic anhydride and then with a propylene oxide α-epoxide at the terminal ends of the intermediate. These steps may be repeated one or more times dependent on the particular intermediate desired, before treatment with bisulfite. The novel di- and poly-sulfosuccinates of the present invention have utility as surfactants particularly for use in the emulsion polymerization of styrene-butadiene or carboxylated styrene-butadiene lattices for use in upholstery backings, carpet backings and related uses.

12 Claims, No Drawings

AROMATIC BASE POLY-SULFOSUCCINATE ESTERS

Our invention is directed to novel di- and other poly-sulfosuccinate ester derivatives at least illustrative ones of which can be represented by the formulae

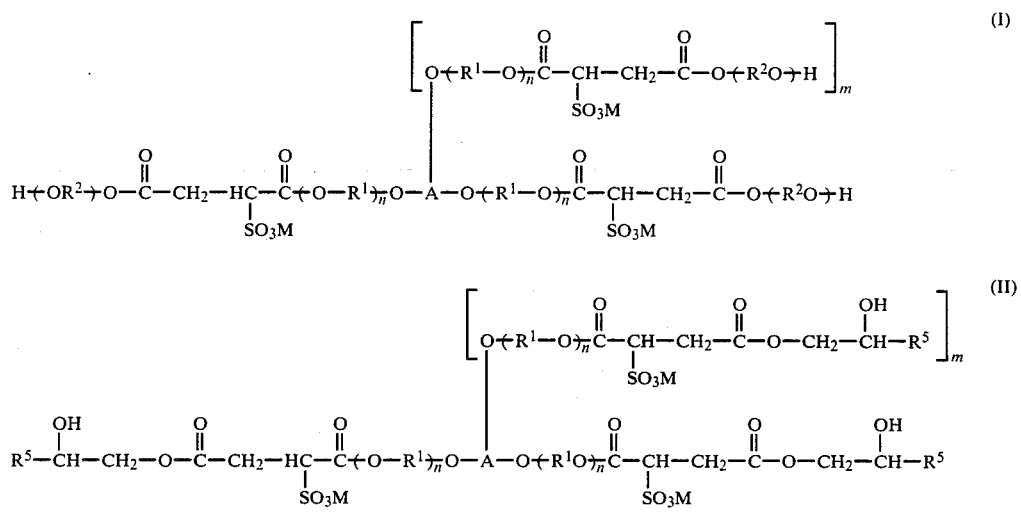

wherein A is the radical of an aromatic di- or other poly-hydroxy compound free from reactive groups other than said hydroxyl groups; $R^1$ is the alkylene moiety of an oxypropylene radical or a mixture of oxypropylene radicals and oxyethylene radicals in which any oxyethylene radicals present constitute up to about 25% by weight of the oxypropylene radicals; $R^2$ is the alkylene moiety of an oxyalkylene radical containing from 3 to 18 carbon atoms or a mixture of such oxyalkylene radicals with oxyethylene radicals in which any oxyethylene radicals present constitute up to 25% of the weight of the oxyalkylene radicals; $R^5$ is alkyl containing from 1 to 16 carbon atoms or phenyl radical; n is an integer from 1 to 2; m is an integer from zero to 2 with the proviso that, when m is zero, the dangling valence is absent; and M is a cation selected from the group of alkali metals, ammonium, alkaline earth metals and water-soluble organic amines.

The cations represented by the letter M will, in most cases, be sodium, but numerous other cations can be used satisfying the above definition of M, illustrative examples of which are potassium, lithium, calcium, magnesium, strontium and barium, or, as noted above, such organic amines as dimethylamine, diethylamine, triethylamine, propylamine, monoisopropylamine, di-isopropylamine, tri-isopropylamine, and commercial mixtures of said isopropylamines; monoisopropanolamine, di-isopropanolamine, triisopropanolamine, and commercial mixtures of said isopropanolamines; ethanolamines such as monoethanolamine, diethanolamine, triethanolamine, and commercial mixtures thereof; polyamines such as aminoethyl ethanolamine, ethylenediamine, diethylenetriamine, hydroxethyl ethylenediamine, and hexamethylenediamine, dimethylbenzylamine, benzylamine, morpholine, etc. Such salts can be prepared from sodium or potassium salts of the novel di- or other poly-sulfosuccinate esters of our present invention by known methathesis techniques.

Certain of the more preferred of the novel compounds of our present invention can be represented by the following formulae

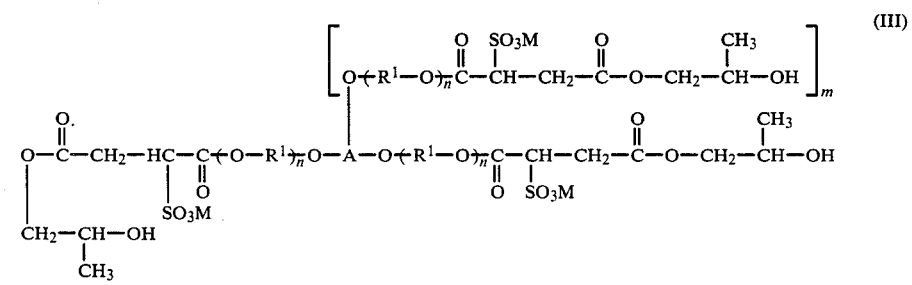

wherein A is the radical of an aromatic di- or poly-hydroxy compound free from reactive groups other than said hydroxyl groups; $R^1$—O is an oxypropylene radical or a mixture of oxypropylene radicals and oxyethylene radicals in which any oxyethylene radicals present constitute up to about 25% by weight of said oxypropylene radicals; n is an integer from 1 to 2; m is an integer from zero to 1; and M is a cation selected from the group of alkali metals, ammonium, alkaline earth metals and water-soluble organic amines.

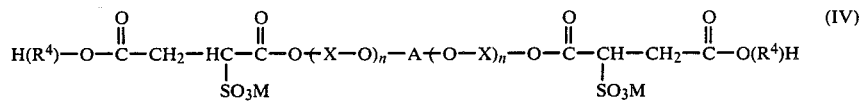

(IV)

wherein A is the radical of a dihydroxy aromatic compound in which the hydroxyl groups are directly connected or linked to an aromatic ring; $R^4$ is an α-epoxide radical containing from 3 to 16 carbon atoms; O—X is a propylene oxide α-epoxide radical; and M is a cation selected from the group of alkali metals, ammonium, alkaline earth metals and water-soluble organic amines; and n is an integer from 1 to 2.

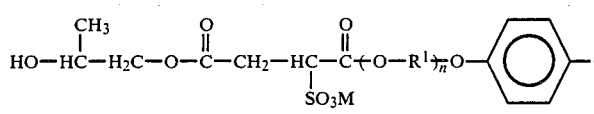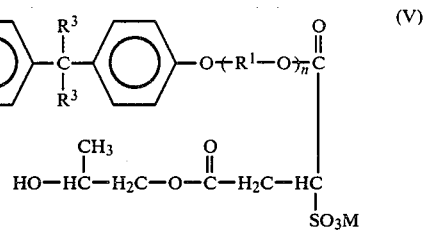

(V)

wherein $R^1$—O— is an α-epoxide propylene oxide radical; $R^3$ is methyl or ethyl; n is an integer from 1 to 2; and M is a cation selected from the group of alkali metals, ammonium, alkaline earth metals and water-soluble organic amines.

Sulfosuccinate esters and, more specifically, sulfosuccinate diesters, are known to the art, being disclosed, for instance, in numbers of U.S. Patents, illustrative of which are U.S. Pat. Nos. 2,028,091; 2,176,423; 2,507,030; 2,887,504; 3,002,994; 3,481,973; 3,640,842; 4,117,237 and 4,154,955. However, so far as we are aware, there has been no prior disclosure nor any suggestion in the foregoing patents or anywhere else of the novel compounds of our present invention.

The novel compounds of our invention are conveniently and most desirably prepared from, as a starting material, an aromatic di- or other poly-hydroxy compound, particularly an aromatic dihydroxy compound in which the hydroxyl groups are directly connected or linked to separate aromatic rings of the aromatic dihydroxy compound, and wherein said aromatic dihydroxy compound is free from any reactive groups other than said hydroxyl groups. Illustrative and especially advantageous embodiments of such starting aromatic dihydroxy compounds are Bisphenol A or Bisphenol S. The process for the preparation of the compounds of our invention will be described hereafter, for convenience, in terms of using Bisphenol A as the starting material, but it will be understood, as will be described hereafter, that other aromatic di- and poly-hydroxy compounds can be used in place of Bisphenol A as the starting material.

Bisphenol A is optionally, but preferably, initially mixed with a small proportion, e.g. about 0.05 to 0.5 or 1% by weight, of an inorganic hydroxide or a basic catalyst, such as an alkaline material, for instance, KOH or NaOH, in the form of a strong aqueous solution, followed by gradually passing into said mixture, below the surface thereof, desirably at somewhat elevated temperatures, so that said mixture is in a liquid or molten condition, propylene oxide, for a period of time, generally a few hours, to produce the desired propoxylate. The number of moles of propylene oxide per mole of Bisphenol A is within the range of 1 to 2, generally speaking, and sufficient propylene oxide is added to introduce into the molecule a slight excess, say about 1.2 to about 1.3 moles of propylene oxide for reaction with each of the two hydroxyl groups of the Bisphenol A to produce the intermediate propoxylated Bisphenol A.

Where a basic catalyst is used in the initial propoxylation of the Bisphenol A, and the subsequent propoxylation step or steps in the preparation of the products of our present invention, in place of potassium hydroxide or sodium hydroxide, other catalysts which can be used are, by way of illustration, sodium carbonate, potassium carbonate, triethylamine, tri-isopropylamine, tetramethyl ammonium hydroxide, tetraethyl ammonium hydroxide, benzyl trimethyl ammonium hydroxide, and benzyl triethyl ammonium hydroxide.

To the resulting propoxylate, though viscous but stirrable, maleic anhydride is added, under elevated temperature and under conditions of stirring or agitation, in proportions such as to esterify free hydroxyl groups to form two maleic acid mono-ester linkages in the molecule, said molecule also containing two free carboxyl groups resulting from the reaction of the propoxylated Bisphenol A with the maleic anhydride, one carboxyl group of each mole of the maleic anhydride esterifying a free hydroxyl group resulting from the prior propoxylation. Then, into said resulting dicarboxylic ester compound, an additional amount of propylene oxide is gradually added over a period of time by passing it, with stirring or agitation and at an elevated temperature, into the liquid or molten body of said dicarboxylic acid ester until the acidity of the reaction mixture is very substantially reduced, for instance, to the order of about 0.003 to 0.008 me/g. Then to the resulting polyester, for instance, tetraester, there is added or admixed therewith an aqueous solution of a bisulfite, such as sodium bisulfite or ammonium bisulfite or an organic amine bisulfite, desirably at somewhat elevated temperatures to introduce sulfonate radicals into the molecule.

Where the novel compounds of our present invention are to be produced in the form of amine salts of the di- or other poly-sulfosuccinate ester, it is convenient initially in carrying out the introduction of the sulfonic groups into the molecule, to react the di- or other polymaleic acid ester intermediate with a solution containing an organic amine, sufficient water to provide a reaction medium and containing dissolved sulfur dioxide to form a sulfite of said organic amine, and a water-miscible alcohol, for instance, methyl alcohol, ethyl alcohol, n-propanol or isopropyl alcohol, whereby to produce a substantially anhydrous organic amine salt of the novel sulfosuccinic acid di- or poly-esters. For best results, in carrying out such reaction, for each mole of said di- or other poly-ester, the solution reacted therewith should contain about 1 mole or slightly more of organic amine or amines, and about 1 mole of water containing about 1 mole of sulfur dioxide for each maleic acid ester group in the molecule of the intermediate compound.

In the preparation of the novel compounds of our invention by the foregoing method, it is important, in order to obtain said compounds, that the sequence of steps noted above be followed, that is, that the maleic acid mono-ester of the propoxylated Bisphenol A first be provided or prepared after which the esterification with maleic anhydride is carried out, followed by the next propoxylation or oxyalkyation step, and then, lastly, the reaction with the aqueous bisulfite to introduce the sulfonic group into the molecule. Thus, for instance, if the propylene oxide is first reacted with the maleic anhydride and then with the Bisphenol A followed by the reaction with the aqueous bisulfite, the products of or contemplated by the present invention are not obtained.

In a variant aspect of our invention, but, nevertheless within the scope thereof, in the production of the novel compounds of our invention, again in terms of the use, for convenience, of Bisphenol A as the starting material and propylene oxide as the initial and subsequent oxyalkyation agent, the following variant procedure can be carried out with the resultant specifically different final compound. After the Bisphenol A is propoxylated with propylene oxide, then reacted with maleic anhydride, and then again propoxylated with propylene oxide, the resulting intermediate compound, prior to reaction with the bisulfite, is again reacted with maleic anhydride to introduce additional maleic acid ester linkages and then again reacted with propylene oxide, after which the sulfonate groups are introduced into the molecule by reaction with aqueous bisulfite salts. An illustrative compound that is obtained by such procedure is shown by the compound (14) in the list of compounds set forth hereafter.

While, from a commercial standpoint and other considerations as well, it is desired to utilize Bisphenol A as the starting dihydroxy aromatic compound in the preparation of the novel di- and other poly-sulfosuccinate ester compounds of our present invention, isomers of Bisphenol A and Bisphenol S can be used as well as such illustrative compounds as 2,2-Bis(4-hydroxyphenyl)butane; 4,4'-dihydroxybenzophenone; Bis-(4-hydroxyphenyl)ethane; 2,2-Bis(4-hydroxyphenyl)pentane; 1,5-dihydroxynaphthalene; hydrogenated Bisphenol A; hydrogenated Bisphenol S; hydrogenated isomers of said bisphenols; and such compounds as are represented by the formula

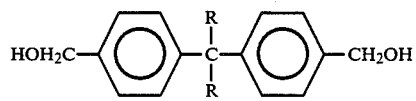

where R is $C_1$ to $C_3$ alkyl. In place of the

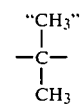

moiety of Bisphenol A, such moiety can be replaced by

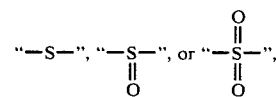

so that the starting aromatic dihydroxy compound is

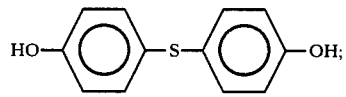

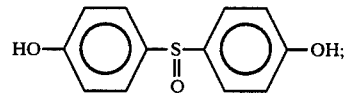

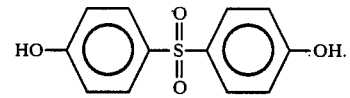

Furthermore, as starting materials, in place of the aforesaid types of aromatic dihydroxy compounds, there can be used trimethylol phenol compounds, or polymeric methylene condensation products of said trimethylol phenol compounds, which may initially be reacted with propylene oxide and thus used as intermediates in the production of the novel poly-sulfosuccinate compounds of our invention. Such trimethylol phenol compounds can be represented by the following formula, and are disclosed as such, for instance, in U.S. Pat. Nos. 3,063,964 and 3,682,845.

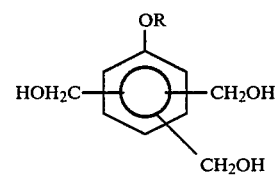

wherein R is hydrogen, or alkyl or alkenyl groups each containing not more than 5 carbon atoms. Ethylene oxide and propylene oxide adducts are also shown in the aforesaid U.S. Pat. No. 3,682,845 and are also disclosed in German Pat. Nos. 1,161,686 and 1,162,070 referred to in said U.S. Pat. No. 3,682,845.

As indicated above, while, in the first propoxylation step, the Bisphenol A is reacted with propylene oxide, a part of the propylene oxide can be replaced by ethylene oxide. In this situation, the ethylene oxide can be admixed with the propylene oxide and the resulting mixture can be reacted with the Bisphenol A. Alternatively, the selected amounts of propylene oxide and ethylene oxide can be reacted sequentially in either order with the Bisphenol A. However, in those cases where ethylene oxide is used, it should be used in minor proportions in relation to the propylene oxide, not to exceed 25% by weight of the propylene oxide.

In the final oxyalkylation step in the production of the compounds of our invention, that is, just preceding the introduction into the molecule of the sulfonate groups by reaction with the aqueous bisulfite, propylene oxide is most desirably used as the oxyalkylating agent. However, in place of or in addition to propylene oxide, other α-epoxides can be used containing more than 3 carbon atoms, for instance, butylene oxides such as 1,2-butylene oxide, pentylene epoxides, hexylene epoxides, glycidyl epoxide, heptylene epoxides, octylene epoxides, dodecylene epoxides, and $C_{16}$–$C_{18}$ olefin oxides or epoxides and, also, styrene epoxides. Most of the α-epoxides in which the vicinal carbons are terminal can be represented by the formula

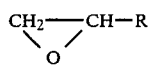

where R is an alkyl radical, and wherein, in the case of propylene oxide, R is $CH_3$. In this final alkoxylation step, as in the case of the initial propoxylation step, ethylene oxide can be employed in conjunction with propylene oxide and/or the higher α-epoxides, used in admixture or sequentially, but, again, the amount of ethylene oxide, if used, should not be in excess of 25% of the weight of the propylene oxide and/or the higher α-epoxides. Indeed, in the case of the use of ethylene oxide in both the initial propoxylation step and the final oxyalkylation step, the ethylene oxide content is preferably used in amounts not in excess of about 15 to 20% instead of the aforementioned upper amount of 25%.

In the aforesaid variants or modifications, in which a minor amount of ethylene oxide is used in conjunction or together with propylene oxide in the first propoxylation step, or in conjunction or together with propylene oxide or higher α-epoxides in the second or subsequent propoxylation or oxyalkylation step or steps, the properties of the final compounds are modified to a certain extent which, in some cases, results in improving the properties of said compounds for their intended uses.

Illustrative examples of the novel compounds of our invention are the following:

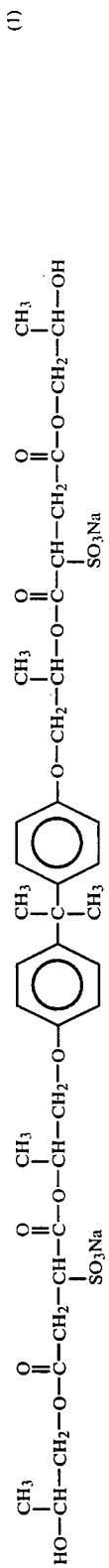 (1)
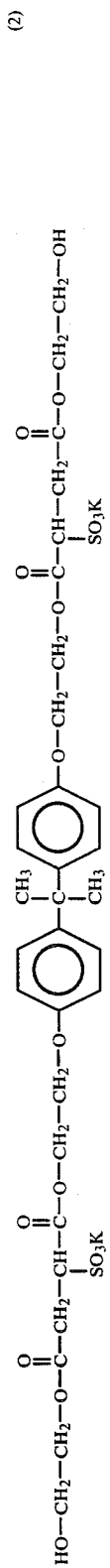 (2)
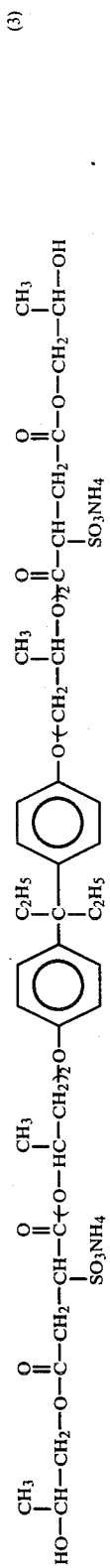 (3)
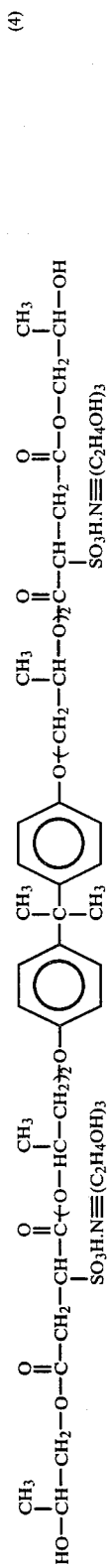 (4)
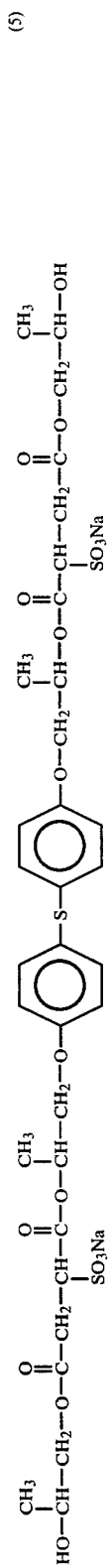 (5)
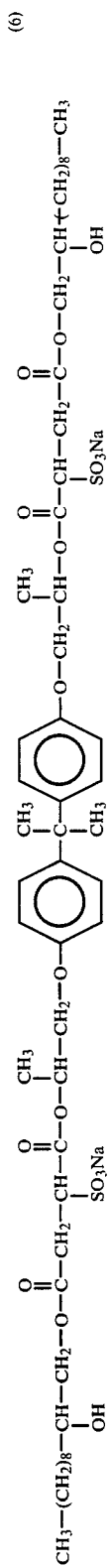 (6)
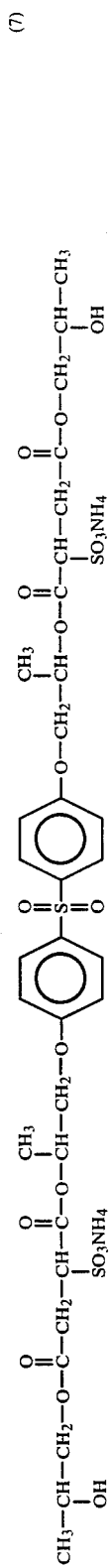 (7)
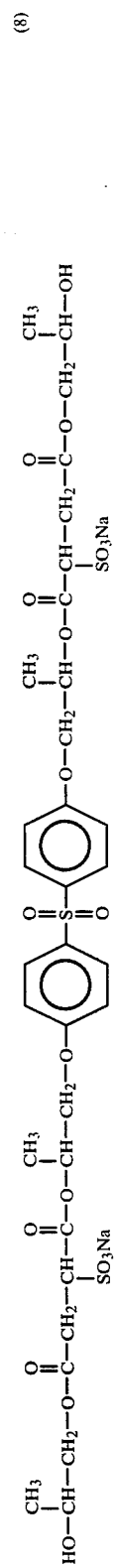 (8)
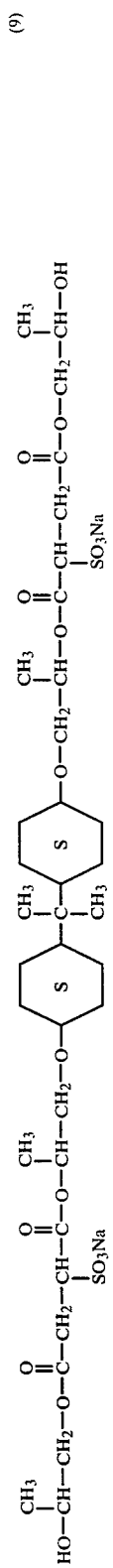 (9)

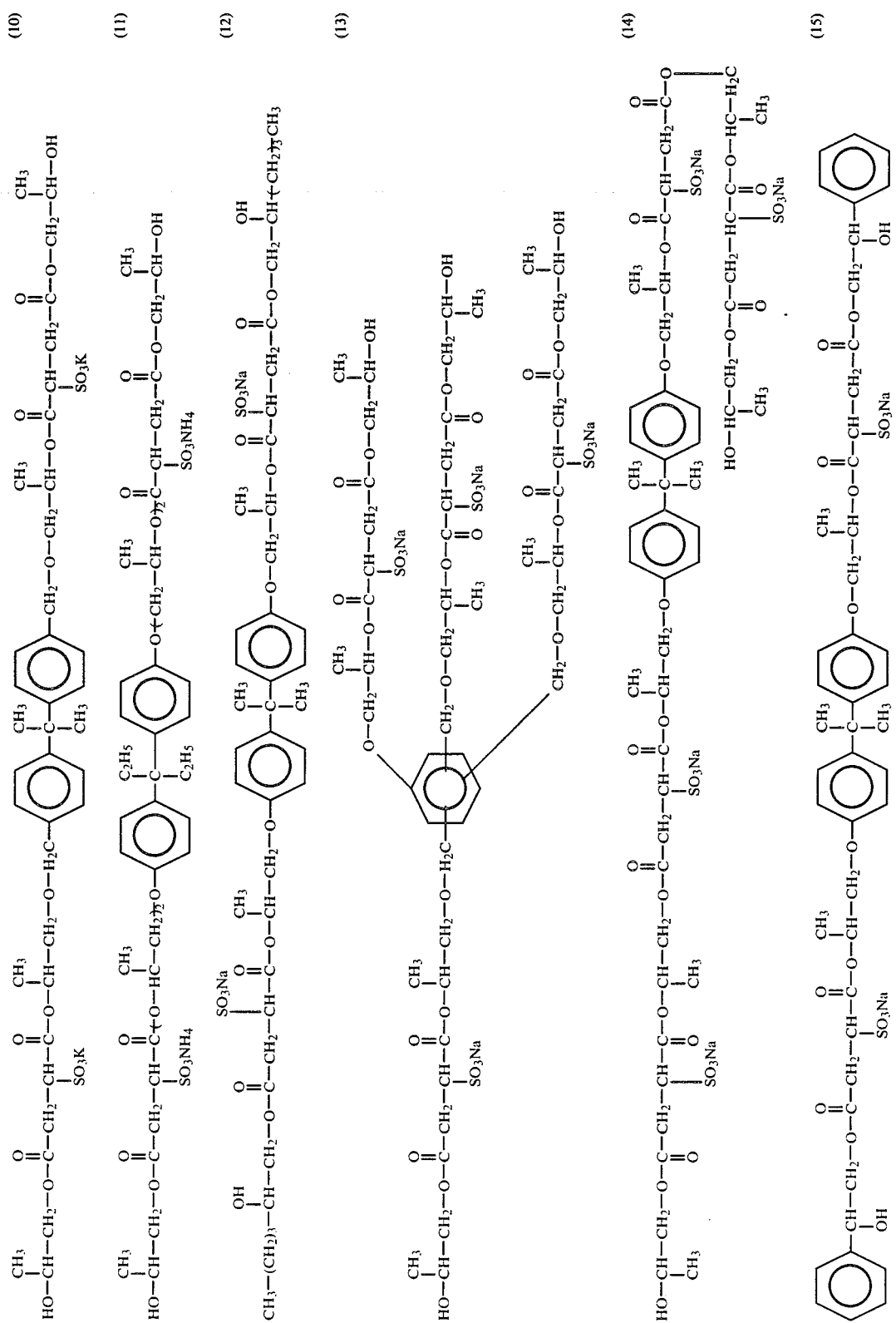

The following examples are illustrative of the preparation of typical compounds of our present invention. All temperatures recited are in degrees Centigrade.

EXAMPLE A

To 257 g of Bisphenol A (1.13 moles) there is added 2 g of KOH flakes, followed by the gradual addition of 144 g of propylene oxide (2.48 moles) at about 110°-160° over a period of approximately 6 hours. To the resulting viscous but stirrable propoxylate 225 g of maleic anhydride (2.3 moles) is added and the mixture is heated at 90°-110° for approximately 2.5 hours, at which time the acidity is 3.67 me/g. To the resulting obtained diester 174 g of propylene oxide (3 moles) is gradually added at about 95°-120° over a period of approximately 3 hours, at the end of which time the acidity is 0.005 me/g. The excess propylene oxide is removed by vacuum at the same temperature. To the resulting tetraester produced, there is added 581 g of a 42% aqueous sodium bisulfite solution (2.34 moles), at about 95°-110°, over a period of approximately 2 hours and under conditions of agitation. A somewhat viscous, reddish-yellow solution is obtained which contains about 0.1% of the sulfite and about 75% solids. The solids comprise essentially a compound corresponding to that of the above formula (1). It can be recovered readily by evaporation of the water, if desired, but it is preferred to produce the composition in the form of an aqueous solution since, in use, it is commonly employed in the form of an aqueous solution.

EXAMPLE B

To 257 g of Bisphenol A (1.13 moles) there is added 2 g of KOH flakes, followed by the gradual addition of 144 g of propylene oxide (2.48 moles) at about 110°-160° over a period of approximately 6 hours. To the resulting viscous but stirrable propoxylate 225 g of maleic anhydride (2.3 moles) is added and the mixture is heated at 90°-110° for approximately 2.5 hours, at which time the acidity is 3.67 me/g. To the resulting obtained diester 343 g of "Epoxide 7" ($C_{8-10}$ based glycidyl epoxide; 1.5 moles) is added at 90°-110° and in about 3 hours the acidity is 1.1 me/g. Then 87 g of propylene oxide (1.5 moles) is gradually added under substantially the same time and temperature conditions, thereby forming the tetraester. The acidity is 0.005 me/g. To the tetraester produced, there is added 581 g of aqueous 42% sodium bisulfite solution (2.34 moles) at about 95°-100° and over a period of approximately 2 hours and under conditions of agitation. The final reaction product is then diluted with 1610 g of water to yield a 40% solution of the disulfosuccinate, containing 0.05% of free sulfite.

EXAMPLE C

Example A is carried out with the exception that, in place of Bisphenol A, 260 g of

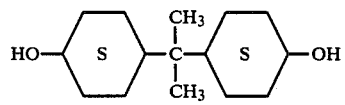

is used, namely, hydrogenated Bisphenol A in which the aromatic rings are saturated. The compound corresponding to formula (8) results.

EXAMPLE D

Example A is carried out with the exception that, in the second propoxylation step, i.e., after the esterification with the maleic anhydride, instead of using propylene oxide, 3 moles of the α-epoxide butylene oxide is utilized. The final compound can be recovered by elimination of the water by evaporation of said water or, as indicated, it is preferably used in the form of its aqueous solution.

EXAMPLE E

Example A is carried out with the exception that, in place of the first propoxylation with propylene oxide, there is used in such propoxylation step a mixture of 130 g of propylene oxide and 14 g of ethylene oxide.

The compounds of the present invention are particularly useful in emulsion polymerization processes for the production of polymers, copolymers and synthetic rubbers, particularly for the production of carboxylated or carbethoxylated styrene-butadiene latices. In such emulsion polymerization processes, the compounds of our invention are used in small proportions, generally of the order of about 0.5 to 2%, to provide proper surface tension characteristics and suitable particle sizes for use of said latices in upholstery backing, carpet backing and the like. While such emulsion polymerization procedures broadly are, per se, well known to the art, the following recipe is illustrative of the use of the compounds of our invention therein. It may be noted that it has heretofore been known to the art to utilize certain particular sulfosuccinate compounds in the emulsion polymerization of various monomers and comonomers to produce latices. However, such sulfosuccinates, which are exemplified by the oleic acid amide of isopropanolamine sulfosuccinate (Na salt) and oleic acid amide of monoethanolamine (K salt), as shown in U.S. Pat. Nos. 2,739,136 and 2,739,138, are radically different from the novel di- and other poly-sulfosuccinate compounds of the present invention. In the following Example, all parts listed are by weight.

EXAMPLE F

| | |
|---|---|
| Styrene | 2250 |
| Butadiene-1,3 | 5200 |
| Water (distilled) | 13,400 |
| Sulfole B-8 | 38 |
| Active Product of Example A | 100 |
| $Na_4P_2O_7.H_2O$ ⎫ | 30 |
| Fe $SO_4.7H_2O$ ⎪ | 16 |
| Dextrose ⎬ Activator | 30 |
| K Cl ⎭ | 8 |
| Cumene hydroperoxide | 7.8 |
| Temperature % C. | 3 to 4 |
| Time | 15 |

The preparation of the activator and the manner of carrying out the emulsion of polymerization procedure can be shown in Example 7 of the aforementioned U.S. Pat. No. 2,739,136. No novelty is claimed in recipes for the emulsion polymerization of monomers to produce latices, as they are well known to those versed in the art and are shown in numerous U.S. patents and printed publications, except for the use herein of the novel di- and other poly-sulfosuccinate products of the present invention which are usually employed in amounts of the order of 0.2 to 3 or 4% by weight of the monomers to be polymerized.

We claim:

1. Aromatic base poly-sulfosuccinates corresponding to the following formula

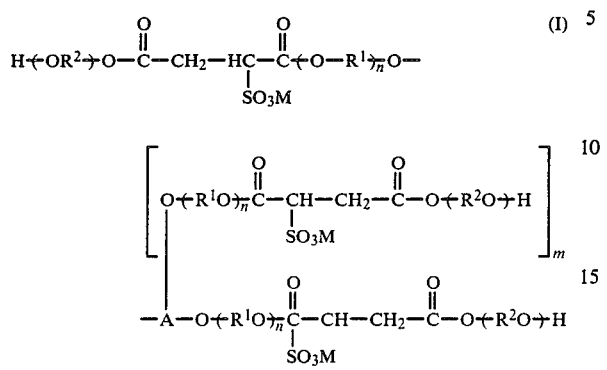

wherein A is a radical derived from an aromatic polyhydroxy compound free from reactive groups other than hydroxy groups selected from the group of:

(a) bisphenols of the formula

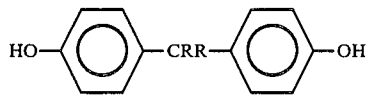

wherein R is $C_1$-$C_3$ alkyl, (b) Bisphenol A derivatives wherein the —C(CH$_3$)$_2$— moiety in Bisphenol A is replaced by —S—,

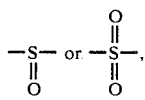

(c) trimethylolphenols of the formula

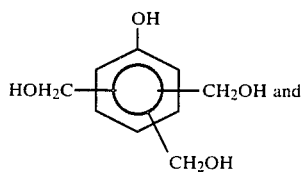

(d)

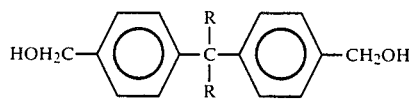

wherein R is $C_1$–$C_3$ alkyl; $R^1$ is an alkylene moiety of an oxypropylene radical or a mixture of oxypropylene radicals and oxyethylene radicals in which any oxyethylene radicals present constitute up to about 25% by weight of the oxypropylene radicals, $R^2$ is an alkylene moiety of an oxyalkylene radical

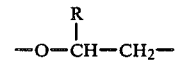

where R is an alkyl radical containing from 1 to 16 carbon atoms; n is an integer from 1 to 2; m is an integer from zero to 2 with the proviso that, when m is zero, the dangling valence is absent; and M is a cation selected from the group of alkali metals, ammonium, alkaline earth metals and water-soluble organic amines.

2. Aromatic base disulfosuccinates according to claim 1 wherein —O—A—O is the radical of a bisphenol selected from the group of Bisphenol A and Bisphenol S, and m is zero.

3. Aromatic base disulfosuccinates according to claim 2 wherein M is sodium.

4. Aromatic base poly-sulfosuccinates corresponding to the following formula

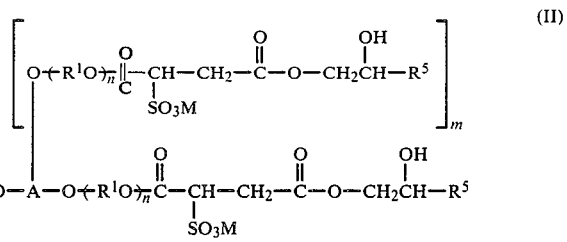

where A is a radical derived from an aromatic polyhydroxy compound free from reactive groups other than hydroxy groups selected from the group of:

(a) bisphenols of the formula

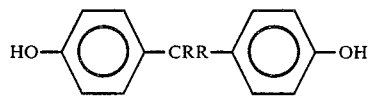

wherein R is $C_1$–$C_3$ alkyl, (b) Bisphenol A derivatives wherein the —C(CH$_3$)$_2$— moiety in Bisphenol A is replaced by —S—,

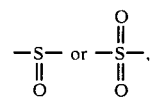

(c) trimethylolphenols of the formula

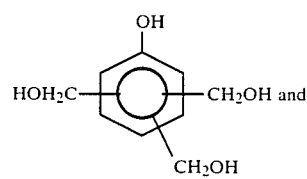

(d)

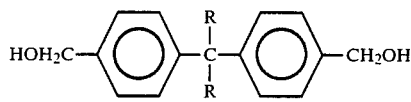

wherein R is $C_1$-$C_3$ alkyl; $R^1$ is an alkylene moiety of an oxypropylene radical or a mixture of oxypropylene radicals and oxyethylene radicals in which any oxyethylene radicals present constitute up to about 25% by weight of said oxypropylene radicals; $R^5$ is alkyl containing from 1 to 16 carbon atoms or a phenyl radical; n is an integer from 1 to 2; m is an integer from zero to 2 with the proviso that, when m is zero, the dangling valence is absent; and M is a cation selected from the group of alkali metals, ammonium, alkaline earth metals and water-soluble organic amines.

5. Aromatic base disulfosuccinates according to claim 4 wherein —O—A—O— is the radical of a bisphenol selected from the group of Bisphenol A and Bisphenol S, and m is zero.

6. Aromatic base disulfosuccinates according to claim 5 wherein M is sodium.

7. Aromatic base disulfosuccinates corresponding to the following formula

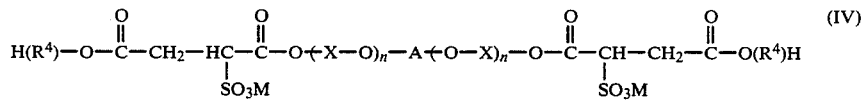 (IV)

wherein A is the radical of a bisphenol of the formula

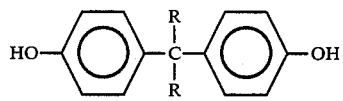

wherein R is $C_1$-$C_3$ alkyl, Bisphenol A derivatives wherein the

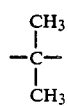

moiety of Bisphenol A is replaced by —S—,

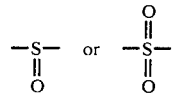

or 1,5-dihydroxynapthalene; $R^4$ is a

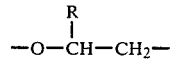

radical derived from an α-epoxide represented by the formula

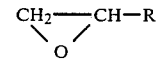

where R is an alkyl radical containing from 1 to 14 carbon atoms; O—X is a

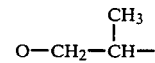

moiety derived from the α-epoxide propylene oxis; M is a cation selected from the group of alkali metals, ammonium, alkaline earth metals and water-soluble organic amines; and n is an integer from 1 to 2.

8. Aromatic base disulfosuccinates according to claim 7 wherein A is the carbon-hydrogen residue of a bisphenol selected from the group of Bisphenol A and Bisphenol S.

9. Aromatic base disulfosuccinates according to claim 8 wherein M is sodium.

10. Aromatic base disulfosuccinates corresponding to the following formula

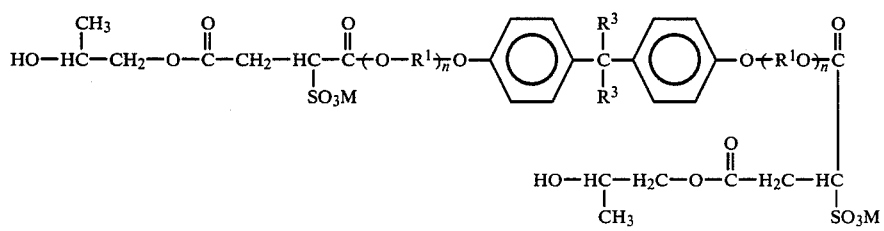

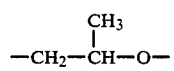

wherein $R^1O$— is a radical derived from the α-epoxide, propylene oxide; $R^3$ is methyl or ethyl; n is an integer from 1 to 2; and M is a cation selected from the group of alkali metals, ammonium, alkaline earth metals and water-soluble organic amines.

11. Aromatic base disulfosuccinates according to claim 10 wherein $R^3$ is methyl.

12. Aromatic base disulfosuccinates according to claim 10 wherein M is sodium.

* * * * *